United States Patent
Smith et al.

(10) Patent No.: US 6,368,800 B1
(45) Date of Patent: Apr. 9, 2002

(54) KITS FOR ISOLATING BIOLOGICAL TARGET MATERIALS USING SILICA MAGNETIC PARTICLES

(75) Inventors: Craig E. Smith, Oregon; Charles K. York, Madison, both of WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/459,502

(22) Filed: Dec. 13, 1999

Related U.S. Application Data (62) Division of application No. 08/785,097, filed on Jan. 21, 1997, now Pat. No. 6,027,945.

(51) Int. Cl.$^7$ .......................... C12Q 1/68; C12P 19/34; G01N 33/553
(52) U.S. Cl. .................. 435/6; 435/287.2; 435/91.1; 435/335; 436/526; 436/527; 536/25.42
(58) Field of Search ............................ 435/6, 526, 335, 435/91.1, 287.2; 536/25.42

(56) References Cited

U.S. PATENT DOCUMENTS

| | | |
|---|---|---|
| 4,233,169 A | 11/1980 | Beall et al. |
| 4,297,337 A | 10/1981 | Mansfield et al. |
| 4,395,271 A | 7/1983 | Beall et al. |
| 4,672,040 A | 6/1987 | Josephson |

(List continued on next page.)

FOREIGN PATENT DOCUMENTS

| | | |
|---|---|---|
| CA | 2223821 | 6/1996 |
| DE | 4307262 A1 | 9/1994 |
| EP | 0757106 A2 | 2/1997 |
| JP | 09327290 | 12/1997 |

(List continued on next page.)

OTHER PUBLICATIONS

Bischoff et al., "Nucleic Acid Resolution By Mixed–Mode Chromatography", *J. Chromatog.* (1984) 296:329–337.

Crowother et al., "High–Performance Liquid Chromatographic Separation of Oligonucleotides and Other Nucleic Acid Constituents on Multifunctional Stationary Phases", *J. Chromatog.* (1983) 282:619–628.

Edwardson et al., "Separation and purification of oligonucleotides using a new bonded–phase packing material", *J. Chromatog.* (19910 545:79–89.

Kirk–Othmer, Encyclopedia of Chemical Technology, (1997)vol. 21, 4th ed., 1997, pp. 1021–1022.

Macherey–Nagel, Macherey–Nagel homepage on the Internet on Jun. 12, 1998, at http://www.machrey–nagel.com.

(List continued on next page.)

*Primary Examiner*—Sean McGarry
*Assistant Examiner*—Karen Lacourciere
(74) *Attorney, Agent, or Firm*—Michael Best & Friedrich LLP; Gary J. Frenchick (57) ABSTRACT

The present invention provides methods for isolating biological target materials, particularly nucleic acids, such as DNA or RNA or hybrid molecules of DNA and RNA, from other substances in a medium using silica magnetic particles. The methods of the present invention involve forming a complex of the silica magnetic particles and the biological target material in a mixture of the medium and particles, separating the complex from the mixture using external magnetic force, and eluting the biological target material from the complex. The preferred embodiments of magnetic silica particles used in the methods and kits of the present invention are capable of forming a complex with at least 2 μg of biological target material per milligram of particle, and of releasing at least 60% of the material from the complex in the elution step of the method. The methods of the present invention produce isolated biological target material which is substantially free of contaminants, such as metals or macromolecular substances, which can interfere with further processing or analysis, if present.

24 Claims, 5 Drawing Sheets

U.S. PATENT DOCUMENTS

| | | |
|---|---|---|
| 4,683,202 A | 7/1987 | Mullis |
| 4,695,393 A | 9/1987 | Whitehead et al. |
| 4,699,717 A | 10/1987 | Riesner et al. |
| 4,767,670 A | 8/1988 | Cox et al. |
| 5,057,426 A | 10/1991 | Henco et al. |
| 5,075,430 A | 12/1991 | Little |
| 5,076,950 A | 12/1991 | Ullman et al. |
| 5,155,018 A | 10/1992 | Gillespie et al. |
| 5,234,809 A | 8/1993 | Boom et al. |
| 5,346,994 A | 9/1994 | Chomczynski |
| 5,395,498 A | 3/1995 | Gombinsky et al. |
| 5,582,988 A | 12/1996 | Backus et al. |
| 5,610,274 A | 3/1997 | Wong et al. |
| 5,658,548 A | 8/1997 | Padhye et al. |
| 5,681,946 A | 10/1997 | Reeve |
| 5,693,785 A | 12/1997 | Woodward et al. |
| 5,734,020 A | 3/1998 | Wong et al. |
| 5,747,663 A | 5/1998 | Colpan et al. |
| 5,783,686 A | 7/1998 | Gonzalez |
| 5,904,848 A | 5/1999 | Wong et al. |
| 5,945,525 A | 8/1999 | Uematsu et al. |
| 5,990,301 A | 11/1999 | Colpan et al. |
| 6,027,945 A | 2/2000 | Smith et al. |

FOREIGN PATENT DOCUMENTS

| | | | |
|---|---|---|---|
| JP | 09327291 | | 12/1997 |
| WO | WO 83/03363 | | 10/1983 |
| WO | WO 95/06652 | | 3/1995 |
| WO | 95/06652 | * | 3/1995 |
| WO | WO 97/29825 | | 8/1997 |
| WO | WO 98/31461 | | 7/1998 |
| WO | WO 98/31840 | | 7/1998 |

OTHER PUBLICATIONS

McLaughlin, L., "Mixed–Mode Chromatography of Nucleic Acids", *Chem Rev* (1989) 89: 309–319.

Northrop et al., "Preparation and Evaluation of a Bimodal Size–Exclusion Chromatography Column Containing a Mixture of Two Silicas of Different Pore Diameter", *Anal. Chem.* (1991) 63:1350–1354.

Promega, Technical Bulletin No. 202 Wizard ® Plus Series 9600 ™ DNA Purification System, (Promega Corp.) (Sep. 1998).

Promega, Technical Bulletin No. 225 Wizard ® Plus SV Minipreps DNA Purification System, (Promega Corp.) (Sep. 1999).

Promega, Technical Bulletin No. 259 Wizard ® PureFection Plasmid DNA Purification System, (Promega Corp.) (Sep. 1999).

QuantiBlot, QuantiBlot Human DNA Quantitation System, PE Applied Biosystems, Feb. 5, 1996, pp. 1–5 (http://ww.pebio.com/fo/773503/773503. html).

Chapter 2 (DNA) and Chapter 4 (RNA) of F. Ausubel et al., eds., *Current Protocols in Molecular Biology*, Wiley–Interscience, New York (1993).

Marko et al., *Anal. Biochem.* 121, pp. 382–387 (1982).

Vogelstein et al., *Proc. Natl. Acad. Sci.* (USA) 76, pp. 615–619 (1979).

Boom et al., *J. Clin Microbiol.* 28, pp. 495–503 (1990).

Chen et al., *Anal Biochem.* 101, pp. 339–341 (1980).

*Kurt–Othmer Encyclopedia of Chemical Technology*, vol. 6, 4th ed., Mary Howe–Grant, ed., John Wiley & Sons, pub., 1993, pp. 773–775.

Wirth et al., *Science* 275, pp. 44–47 (1997).

Database CAS online, AN 126:182277, Uematsu et al. 'Magnetic carriers for the separation of nucleic acids and methods of using them'. Jpn. Kokai Tokkyo Koho, 9 pp. Jan. 21 1997, abstract (EP 0 757 106 A2 corresponding thereto in English is enclosed).

Database CAS online, AN 126:86772, Kleiber et al. 'Magnetic particles and their use for isolation of biological materials'. Ger. Offen., 9 pp. Dec. 12, 1996, abstract.

\* cited by examiner

KITS FOR ISOLATING BIOLOGICAL TARGET MATERIALS USING SILICA MAGNETIC PARTICLES

CROSS-REFERENCE TO RELATED APPLICATIONS

This application is a divisional of U.S. patent application Ser. No. 08/785,097, filed Jan. 21, 1997, now U.S. Pat. No. 6,027,945. Reference is made to concurrently filed U.S. patent application Ser. No. 08/786,600, entitled "Silica Adsorbent on Magnetic Substrate", filed concurrently therewith on Jan. 21, 1997 (international counterpart published as WO 98/31461 on Jul. 23, 1998).

FIELD OF THE INVENTION

The present invention relates to methods for separating or isolating a biological target material from other substances in a medium to produce an isolated material of sufficient purity for further processing or analysis. The present invention particularly relates to methods for separating or isolating biological target materials using magnetically responsive particles capable reversibly binding the material. The present invention more specifically relates to methods for separating or isolating biological target materials using at least one magnetically responsive particle comprising silica or a silica derivative such as silica gel which reversibly binds the biological target material thereof.

BACKGROUND OF THE INVENTION

Many molecular biological techniques such as reverse transcription, cloning, restriction analysis, and sequencing involve the processing or analysis of biological materials. These techniques generally require that such materials be substantially free of contaminants capable of interfering with such processing or analysis procedures. Such contaminants generally include substances that block or inhibit chemical reactions, (e.g. nucleic acid or protein hybridizations, enzymatically catalyzed reactions, and other types of reactions, used in molecular biological techniques), substances that catalyze the degradation or depolymerization of a nucleic acid or other biological material of interest, or substances that provide "background" indicative of the presence in a sample of a quantity of a biological target material of interest when the nucleic acid is not, in fact present in the sample. Contaminants also include macromolecular substances from the in vivo or in vitro medium from which a nucleic acid material of interest is isolated, macromolecular substances such as enzymes, other types of proteins, polysaccharides, or polynucleotides, as well as lower molecular weight substances, such as lipids, low molecular weight enzyme inhibitors or oligonucleotides. Contaminants can also be introduced into a target biological material from chemicals or other materials used to isolate the material from other substances. Common contaminants of this last type include trace metals, dyes, and organic solvents.

Obtaining DNA or RNA sufficiently free of contaminants for molecular biological applications is complicated by the complex systems in which the DNA or RNA is typically found. These systems, e.g., cells from tissues, cells from body fluids such as blood, lymph, milk, urine, feces, semen, or the like, cells in culture, agarose or polyacrylamide gels, or solutions in which target nucleic acid amplification has been carried out, typically include significant quantities of contaminants from which the DNA or RNA of interest must be isolated before being used in a molecular biological procedure.

Conventional protocols for obtaining DNA or RNA from cells are described in the literature. See, e.g. Chapter 2 (DNA) and Chapter 4 (RNA) of F. Ausubel et al., eds., *Current Protocols in Molecular Biology*, Wiley-Interscience, New York (1993). Conventional DNA isolation protocols generally entail suspending the cells in a solution and using enzymes and/or chemicals, gently to lyse the cells, thereby releasing the DNA contained within the cells into the resulting lysate solution. For isolation of RNA, the conventional lysis and solubilization procedures include measures for inhibition of ribonucleases and contaminants to be separated from the RNA including DNA.

Many conventional protocols in use today also generally entail use of phenol or an organic solvent mixture containing phenol and chloroform to extract additional cellular material such as proteins and lipids from a conventional lysate solution produced as described above. The phenol/chloroform extraction step is generally followed by precipitation of the nucleic acid material remaining in the extracted aqueous phase by adding ethanol to that aqueous phase. The precipitate is typically removed from the solution by centrifugation, and the resulting pellet of precipitate is allowed to dry before being resuspended in water or a buffer solution for further processing or analysis.

Conventional nucleic acid isolation procedures have significant drawbacks. Among these drawbacks are the time required for the multiple processing steps necessary in the extractions and the dangers of using phenol or chloroform. Phenol causes severe burns on contact. Chloroform is highly volatile, toxic and flammable. Those characteristics require that phenol be handled and phenol/chloroform extractions be carried out in a fume hood.

Another undesirable characteristic of phenol/chloroform extractions is that the oxidation products of phenol can damage nucleic acids. Only freshly redistilled phenol can be used effectively, and nucleic acids cannot be left in the presence of phenol. Generally also, multi-step procedures are required to isolate RNA after phenol/chloroform extraction. Ethanol (or isopropanol) precipitation must be employed to precipitate the DNA from a phenol/chloroform-extracted aqueous solution of DNA and remove residual phenol and chloroform from the DNA. Further, ethanol (or isopropanol) precipitation is required to remove some nucleoside triphosphate and short (i.e., less than about 30 bases or base pairs) single or double-stranded oligonucleotide contaminants from the DNA. Moreover, under the best circumstances such methods produce relatively low yields of isolated nucleic acid material and/or isolated nucleic acid material contaminated with impurities.

There is a need recognized in the art for methods, that are simpler, safer, or more effective than the traditional phenol/chloroform extraction/ethanol precipitation methods to isolate DNA and/or RNA sufficiently for manipulation using molecular biological procedures.

Fractionation of DNA recovered from cells according to size is required for many molecular biological procedures. Such fractionation is typically accomplished by agarose or polyacrylamide gel electrophoresis. For analysis or treatment by a molecular biological procedure after fractionation, the DNA in the fraction(s) of interest must be separated from contaminants, such as agarose, other polysaccharides, polyacrylamide, acrylamide, or acrylic acid, in the gel used in such electrophoresis. Thus, there is also a need in the art for methods to accomplish such separations.

Methods for amplifying nucleic acids or segments thereof, such as the well known polymerase chain reaction (PCR) process (see, e.g., U.S. Pat. No. 4,683,202), yield solutions of complex mixtures of enzymes, nucleoside triphosphates, oligonucleotides, and other nucleic acids. Typically, the methods are carried out to obtain an highly increased quantity of a single nucleic acid segment ("target segment"). Often it is necessary to separate this target segment from other components in the solution after the amplification process has been carried out. Thus there is a further need in the art for simple methods to accomplish these separations.

Silica materials, including glass particles, such as glass powder, silica particles, and glass microfibers prepared by grinding glass fiber filter papers, and including diatomaceous earth, have been employed in combination with aqueous solutions of chaotropic salts to separate DNA from other substances and render the DNA suitable for use in molecular biological procedures. See U.S. Pat. No. 5,075,430 and references cited therein, including Marko et al., Anal. Biochem. 121, 382–387 (1982) and Vogelstein et al., Proc. Natl. Acad. Sci. (USA) 76, 615–619 (1979). See also Boom et al., J. Clin. Microbiol. 28, 495–503 (1990). With reference to intact glass fiber filters used in combination with aqueous solutions of a chaotropic agent to separate DNA from other substances, see Chen and Thomas, Anal. Biochem. 101, 339–341 (1980). Vogelstein et al., supra, suggest that silica gel is not suitable for use in DNA separations. With regard to separation of RNA using silica materials and chaotropic agents, see Gillespie et al., U.S. Pat. No. 5,155,018.

Glass particles, silica particles, silica gel, and mixtures of the above have been configured in various different forms to produce matrices capable of reversibly binding nucleic acid materials when placed in contact with a medium containing such materials in the presence of chaotropic agents. Such matrices are designed to remain bound to the nucleic acid material while the matrix is exposed to an external force such as centrifugation or vacuum filtration to separate the matrix and nucleic acid material bound thereto from the remaining media components. The nucleic acid material is then eluted from the matrix by exposing the matrix to an elution solution, such as water or an elution buffer. Numerous commercial sources offer silica-based matrices designed for use in centrifugation and/or filtration isolation systems. See, e.g. Wizard™ DNA purification systems line of products from Promega Corporation (Madison, Wis., U.S.A.); or the QiaPrep™ line of DNA isolation systems from Qiagen Corp. (Chatsworth, Calif., U.S.A.)

Magnetically responsive particles (hereinafter, "magnetic particles") have conventionally been used to isolate and purify polypeptide molecules such as proteins or antibodies. In recent years, however, magnetic particles and methods for using magnetic particles have been developed for the isolation of nucleic acid materials. Several different types of magnetic particles designed for use in nucleic acid isolation are described in the literature, and many of those types of particles are available from commercial sources. Such magnetic particles generally fall into either of two categories, those designed to reversibly bind nucleic acid materials directly, and those designed to do so through at least one intermediary substance. The intermediary substance is referred to herein as a "label."

The magnetic particles designed to bind nucleic acid materials indirectly are generally used to isolate a specific nucleic acid material, such as mRNA, according to the following basic isolation procedure. First, a medium containing a nucleic acid material is placed in contact with a label capable of binding to the nucleic acid material of interest. For example, one such commonly employed label, biotinylated oligonucleotide deoxythymidine (oligo-dT), forms hydrogen bonds with the poly-adenosine tails of mRNA molecules in a medium. Each label so employed is designed to bind with a magnetically responsive particle, when placed into contact with the particle under the proper binding conditions. For example, the biotin end of a biotinylated oligo-dT/mRNA complex is capable of binding to streptavidin moieties on the surface of a streptavidin coated magnetically responsive particle. Several different commercial sources are available for streptavidin magnetic particles and reagents designed to be used in mRNA isolation using biotinylated oligo-dT as described above. See, e.g. PolyATtract® Series 9600™ mRNA Isolation System from Promega Corporation; or the ProActive™ line of streptavidin coated microsphere particles from Bangs Laboratories (Carmel, Ind., U.S.A.). Magnetic particles and label systems have also been developed which are capable of indirectly binding and isolating other types of nucleic acids, such as double-stranded and single-stranded PCR templates. See, e.g. BioMag™ superparamagnetic particles from Advanced Magnetics, Inc. (Cambridge, Mass., U.S.A.)

Indirect binding magnetic separation systems for nucleic acid isolation or separation all require at least three components, i.e. magnetic particles, a label, and a medium containing the nucleic acid material of interest. The label/nucleic acid binding reaction and label/particle binding reaction often require different solution and/or temperature reaction conditions from one another. Each additional component or solution used in the nucleic acid isolation procedure adds to the risk of contamination of the isolated end product by nucleases, metals, and other deleterious substances.

A few types of magnetic particles have also been developed for use in the direct binding and isolation of biological materials, particularly nucleic acid. One such particle type is a magnetically responsive glass bead, preferably of a controlled pore size. See, e.g. Magnetic Porous Glass (MPG) particles from CPG, Inc. (Lincoln Park, N.J., U.S.A.); or porous magnetic glass particles described in U.S. Pat. Nos. 4,395,271; 4,233,169; or 4,297,337. Nucleic acid material tends to bind so tightly to glass, however, that it can be difficult to remove once bound thereto. Therefore, elution efficiencies from magnetic glass particles tend to be low compared to elution efficiencies from particles containing lower amounts of a nucleic acid binding material such as silica.

A second type of magnetically responsive particles designed for use in direct binding and isolation of biological materials, particularly nucleic acid, are particles comprised of agarose embedded with smaller ferromagnetic particles and coated with glass. See, e.g. U.S. Pat. No. 5,395,498. A third type of magnetically responsive particle, a particle capable of directly bind enzymes, proteins, hormones, or antibodies, is produced by incorporating magnetic materials into the matrix of polymeric silicon dioxide compounds. See, e.g. German Patent No. DE 43 07 262 A1. The latter two types of magnetic particles, the agarose particle and the polymeric silicon dioxide matrix, tend to leach iron into a medium under the conditions required to bind biological materials directly to each such magnetic particle. It is also difficult to produce such particles with a sufficiently uniform and concentrated magnetic capacity to ensure rapid and efficient isolation of nucleic acid materials bound thereto.

What is needed is a method for isolating biological entities, particularly nucleic acids, using a magnetically responsive particle capable of rapidly and efficiently directly isolating such entities sufficiently free of contaminants to be used in molecular biology procedures.

SUMMARY OF THE INVENTION

Briefly, in one aspect, the present invention comprises a method of isolating a biological target material from other materials in a medium by:

providing a medium including the biological target material;

providing silica magnetic particles;

forming a complex of the silica magnetic particles and the biological target material by combining the silica magnetic particles and the medium;

removing the complex from the medium by application of an external magnetic field and separating the biological target material from the complex by eluting the biological target material whereby the isolated biological target material is obtained.

In a further aspect, the present invention is a method of isolating a biological target material of interest from other materials in a medium using silica magnetic particles capable of reversibly binding at least 2 micrograms of a biological target material per milligram of silica magnetic particles, and of releasing at least 60% of the biological target material bound thereto. In preferred practices of the present method, at least about 4 micrograms of biological target material per milligram of silica magnetic particle is bound thereto and at least about 75% of the biological target material adhered to the silica magnetic particles is subsequently eluted. The biological target material isolated according to the method of this invention is preferably nucleic acid.

A preferred practice of the method of the present invention comprises the following steps. First, a mixture is formed comprising the medium and the silica magnetic particles. Second, the biological target material is adhered to the silica magnetic particles in the mixture. Third, the silica magnetic particles are removed from the mixture using an external force, most preferably using a magnetic force, and Fourth, at least 60% of the biological target material adhered to the silica magnetic particle is eluted by contacting the particle with an elution solution.

In another aspect, the present invention is a method of isolating plasmid DNA from other materials in a medium using a preferred form of silica magnetic particle, i.e., siliceous-oxide coated magnetic particle, wherein the preferred particles are capable of binding at least 2 micrograms of the plasmid DNA material per milligram of particle, and of releasing at least 60% of the plasmid DNA material bound thereto. A preferred practice of the methods of this aspect of the invention comprise the following steps. First, a mixture is formed comprising the medium including plasmid DNA, the siliceous-oxide coated magnetic particle, and a chaotropic salt. Second, the plasmid DNA is adhered to the siliceous-oxide coated magnetic particle in the mixture. Third, the siliceous-oxide coated magnetic particle is removed from the mixture using an external force, most preferably using a magnetic field. Fourth, at least 60% of the plasmid DNA adhered to the siliceous-oxide coated magnetic particle is eluted by contacting the particle with an elution solution.

In a further aspect, the present invention is a kit for isolating a biological target material from a medium containing the same, the kit comprising an aliquot of siliceous-oxide coated magnetic particles suspended in an aqueous solution in a first container, wherein the particles have the capacity to reversibly bind at least 2 micrograms of the biological target material per milligram of particle. Optionally, the kit may include other components needed to isolate a biological target material from a medium containing the same according to the methods of the present invention.

As used herein, the term "magnetic particles" refers to materials which have no magnetic field but which form a magnetic dipole when exposed to a magnetic field, i.e., materials capable of being magnetized in the presence of a magnetic field but which are not themselves magnetic in the absence of such a field. The term "magnetic" as used in this context includes materials which are paramagnetic or superparamagnetic materials. The term "magnetic", as used herein, also encompasses temporarily magnetic materials, such as ferromagnetic or ferrimagnetic materials with low Curie temperatures, provided that such temporarily magnetic materials are paramagnetic in the temperature range at which silica magnetic particles containing such materials are used according to the present methods to isolate biological materials.

The term "silica magnetic particle" refers to a magnetic particle comprised of silica in the form of silica gel, siliceous oxide, solid silica such as glass or diatamaceous earth, or a mixture of two or more of the above. The term "silica gel" as used herein refers to chromatography grade silica gel, a substance which is commercially available from a number of different sources. Silica gel is most commonly prepared by acidifying a solution containing silicate, e.g. sodium silicate, to a pH of less than 10 or 11 and then allowing the acidified solution to gel. See, e.g. silica preparation discussion in *Kurt-Othmer Encyclopedia of Chemical Technology*, Vol. 6, 4th ed., Mary Howe-Grant, ed., John Wiley & Sons, pub., 1993, pp. 773–775. The term "silica magnetic particle" as used herein preferably refers to particles with the characteristics described above having the capacity to bind at least 2 micrograms of biological target material per milligram of silica magnetic particles and, independently, the capacity to release at least 60% of the biological target material bound thereto in the elution step of the present method. The silica magnetic particles used in the present invention preferably further comprise ferromagnetic material incorporated into a silica gel matrix. The elution step in the isolation methods of this invention are preferably accomplished without substantial contamination of the nucleic acid material by metal or metal compounds (e.g., iron or iron compounds) or other objectionable species originating from the silica magnetic particles.

The term "glass particles" as used herein means particles of crystalline silicas (e.g., α-quartz, vitreous silica), even though crystalline silicas are not formally "glasses" because they are not amorphous, or particles of glass made primarily of silica.

The term "siliceous-oxide coated magnetic particle" or "SOCM particle" is used herein to refer to the most preferred form of silica magnetic particle used in the methods and kits of the present invention. The SOCM particle is comprised of siliceous oxide coating a core of at least one particle of superparamagnetic or paramagnetic material. The SOCM particle used in the present method and kits also has an adsorptive surface of hydrous siliceous oxide, a surface characterized by having silanol groups thereon. Target nucleic acid material, such as DNA or RNA, adhere to the adsorptive surface of the particle while other material, particularly deleterious contaminants such as exonucleases, do not adhere to or co-elute from the particle with the nucleic acid materials. The physical characteristics of the SOCM particle and methods for producing such particles are disclosed in concurrently filed U.S. patent application Ser. No. 08/786,600, entitled "Silica Adsorbent on Magnetic Substrate," the disclosure of which is incorporated by reference herein.

The present invention provides convenient and efficient means for isolating biological target material of interest from a variety of different media. A preferred aspect of the present method described briefly above, wherein magnetic force is used to remove the particles from the media, offers significant advantages over conventional isolation methods wherein a biological target material is reversibly bound to other silica material. Specifically, the magnetic removal step of the method substitutes for vacuum filtration or centrifugation steps required in conventional silica binding and elution isolation methods. It is, therefore, particularly amenable to being automated. Small laboratories or individual researchers frequently must purchase specialized and expensive equipment to carry out such methods, such as a vacuum manifold and vacuum for use in vacuum filtration or a microcentrifuge for centrifugation methods. Contrastingly, magnetic separation of the present invention merely requires a concentrated magnetic field such as is generated from a strong and readily available magnet. Inexpensive apparatuses specifically adapted for use in molecular biology research context are also commercially available, such as the MagneSphere® Technology Magnetic Separation Stand or the PolyATract® Series 9600™ Multi-Magnet (both available from Promega Corporation, Madison, Wis., USA).

The biological target material isolated using the isolation method of the present invention is sufficiently free of contaminating material for additional processing or analysis using standard molecular biology techniques. Applications of the present methods to isolate various different biological target materials from a variety of different media will become apparent from the detailed description of the invention below.

DETAILED DESCRIPTION OF THE INVENTION

The biological target material isolated using the methods of the present invention is preferably a nucleic acid or a protein, more preferably a nucleic acid material such as RNA, DNA, or a RNA/DNA hybrid. When the biological target material isolated using the present methods is a nucleic acid, it is preferably DNA, or RNA including but not limited to plasmid DNA, DNA fragments produced from restriction enzyme digestion, amplified DNA produced by an amplification reaction such as the polymerase chain reaction (PCR), single-stranded DNA, mRNA, or total RNA. The nucleic acid material isolated according to the methods of the present invention is even more preferably a plasmid DNA or total RNA.

Since nucleic acids are the most preferred biological target material isolated using the methods of the present invention, most of the detailed description of the invention below describes this preferred aspect of the present invention. However, the detailed description of this particular aspect of the present invention is not intended to limit the scope of the invention. The present disclosure provides sufficient guidance to enable one of ordinary skill in the art of the present invention to use the methods of the present invention to isolate biological target materials other than nucleic acid materials, e.g., proteins or antibodies.

The present methods of isolating biological target material can be practiced using any silica magnetic particle, but the methods are preferably practiced using the SOCM form of silica magnetic particles. The present methods are also preferably practiced using silica magnetic particles with the following physical characteristics.

The silica magnetic particles used in the methods of this invention may be any one of a number of different sizes. Smaller silica magnetic particles provide more surface area (one per weight unit basis) for adsorption, but smaller particles are limited in the amount of magnetic material which can be incorporated into such particles compared to larger particles. The median particle size of the silica magnetic particles used in the present invention is preferably about 1 to 15 µm, more preferably about 3 to 10 µm, and most preferably about 4 to 7 µm. The particle size distribution may also be varied. However, a relatively narrow monodal particle size distribution is preferred. The monodal particle size distribution is preferably such that about 80% by weight of the particles are within a 10 µm range about the median particle size, more preferably within an 8 µm range, and most preferably within a 6 µm range.

The silica magnetic particle preferably used in the present invention has pores which are accessible from the exterior of the particle. The pores are preferably of a controlled size range sufficiently large to admit a biological target material, e.g., nucleic acid, into the interior of the particle and to bind to the silica gel material on the interior surface of most such pores. The pores of the most preferred form of the silica magnetic particles are designed to provide a large surface area of silica gel material capable of binding a biological target material, particularly nucleic material. The total pore volume of a silica magnetic particle, as measured by nitrogen BET method, is preferably at least about 0.2 ml/g of particle mass. Of the total pore volume measured by nitrogen BET, preferably at least about 50% of the pore volume is contained in pores having a diameter of 600 Å or greater.

The silica magnetic particles may contain substances, such as transition metals or volatile organics, which could adversely affect the utility of isolated biological target material substantially contaminated with such substances. Specifically, such contaminants could affect downstream processing, analysis, and/or use of the such materials, for example, by inhibiting enzyme activity or nicking or degrading the target material itself. Any such substances present in the silica magnetic particles used in the present invention are preferably present in a form which does not readily leach out of the particle and into the isolated biological target material produced according to the methods of the present invention. Iron is one such undesirable contaminant, particularly when the biological target material is a nucleic acid. Iron, in the form of magnetite, is present at the core of a particularly preferred form of the silica magnetic particles of the present invention, i.e. the SOCM particles. Iron has a broad absorption peak between 260 and 270 nanometers (nm). Nucleic acids have a peak absorption at about 260 nm, so iron contamination in a nucleic acid sample can adversely affect the accuracy of the results of quantitative spectrophotometric analysis of such samples. Any iron containing silica magnetic particles used to isolate nucleic acids using the present invention preferably do not produce isolated nucleic acid material sufficiently contaminated with iron for the iron to interfere with spectrophotometric analysis of the material at or around 260 nm.

The most prefered silica magnetic particles used in the methods of the present invention, the SOCM particles, leach no more than 50 ppm, more preferably no more than 10 ppm, and most preferably no more than 5 ppm of transition metals when assayed as follows. Specifically, 0.33 g of the particles (oven dried @ 110° C.) into 20 ml. of 1N HCl aqueous solution (using deionized water). The resulting mixture is then agitated only to disperse the particles. After about 15 minutes total contact time, a portion of the liquid from the mixture is then analyzed for metals content. Any conventional elemental analysis technique may be employed to quantify the amount of transition metal in the resulting liquid, but inductively coupled plasma spectroscopy (ICP) is preferred.

Concurrently filed patent application Ser. No. 08/786,600, entitled "Silica Adsorbent on Magnetic Substrate" incorporated by reference herein, discloses methods for producing SOCM particles suitable for use in the methods and kits of the present invention. The most preferred such method for producing SOCM particles for use in the present invention comprises the general steps of: (1) preparing magnetite core particles by aqueous precipitation of a mixture of $FeCl_2$ and $FeCl_3$. (2) depositing a siliceous oxide coating on the magnetite core particles by exposing a slurry of the particles to a mixture of $SiO_2$ and $Na_2O$ for at least about 45 minutes at a temperature of at least 60° C. and then adding an acid solution to the mixture until the pH is lowered to a pH less than 9, (3) allowing the resulting slurry to age for at least about 15 minutes, preferably while continuing to agitate the slurry, and (4) washing the particles. The deposition and aging steps of the preferred particle production method described above can be repeated to produce multiple layers of siliceous oxide coating over the magnetite core, thus providing additional insurance against leaching of metals from the core into the surrounding environment. SOCM particles produced by the method described above are most preferably treated by being subjected to a mild oxidizing step to further inhibit leaching from the core.

The biological target material isolated using the method of the present invention can be obtained from eukaryotic or prokaryotic cells in culture or from cells taken or obtained from tissues, multicellular organisms including animals and plants; body fluids such as blood, lymph, urine, feces, or semen; embryos or fetuses; food stuffs; cosmetics; or any other source of cells. Some biological target materials, such as certain species of DNA or RNA are isolated according to the present method from the DNA or RNA of organelles, viruses, phages, plasmids, viroids or the like that infect cells. Cells will be lysed and the lysate usually processed in various ways familiar to those in the art to obtain an aqueous solution of DNA or RNA, to which the separation or isolation methods of the invention are applied. The DNA or RNA, in such a solution, will typically be found with other components, such as proteins, RNAs (in the case of DNA separation), DNAs (in the case of RNA separation), or other types of components.

Regardless of the nature of the source of such material, the biological target material to be isolated in the present methods is provided in a medium comprising the biological target material and other species. The biological target material must be present in the medium in a form in which it is available to adhere to the silica magnetic particles in the first step of the method. When the nucleic acid material is contained inside a cell, the cell walls or cell membrane can make the material unavailable for adhesion to the particles. Even if such cells are lysed or sufficiently disrupted to cause the nucleic acid material contained therein to be released into the surrounding solution, cellular debris in the solution could interfere with the adhesion of the nucleic acid material to the silica magnetic particles. Therefore, in cases where the nucleic acid material to be isolated using the methods of the present invention is contained within a cell, the cell is preferably first processed by lysing or disrupting the cell to produce a lysate, and more preferably additionally processed by clearing the lysate of cellular debris (e.g., by centrifugation or vacuum filtration) likely to interfere with adhesion of the nucleic acid material to silica magnetic particles when provided as the medium in the methods of the present invention.

Any one of a number of different known methods for lysing or disrupting cells to release nucleic acid materials contained therein are suitable for use in producing a medium from cells for use in the present invention. The method chosen to release the nucleic acid material from a cell will depend upon the nature of the cell containing the material. For example, in order to cause a cell with a relatively hard cell wall, such as a fungus cell or a plant cell, to release the nucleic acid material contained therein one may need to use harsh treatments such as potent proteases and mechanical shearing with a homogenizer or disruption with sound waves using a sonicator. Contrastingly, nucleic acid material can be readily released from cells with lipid bi-layer membranes such as *E. coli* bacteria or animal blood cells merely by suspending such cells in an aqueous solution and adding a detergent to the solution.

Once the nucleic acid material is released from cells lysed or disrupted as described above, cellular debris likely to interfere with the adhesion of the nucleic acid material to silica magnetic particles can be removed using a number of different known techniques or combination of techniques. The solution of lysed or disrupted cells is preferably centrifuged to remove particulate cell debris. The supernatant is then preferably further processed by adding a second solution to the supernatant which causes a precipitate of additional other material to form, and then removing the precipitate from the resulting solution by centrifugation.

In a particularly preferred aspect of the present method, the nucleic acid material of interest isolated according to the method of the present invention is plasmid DNA initially contained in an *E. coli* bacteria cell. The nucleic acid material is most preferably released from the bacteria cell by addition of an alkaline solution, such as a solution of sodium hydroxide, to form a lysate. The lysate is then preferably further treated by centrifugation to remove cell debris. A neutralizing solution, such as an acidic buffer, is preferably added to the resulting supernatant to form a precipitate of additional potentially interfering material. The precipitate thus formed is preferably removed by centrifugation. The remaining supernatant of cleared lysate is the medium provided in the first step of this particularly preferred aspect of the present method.

The medium provided in the first step of the method of this invention need not contain nucleic acid material released directly from cells. The nucleic acid material can be the product of an amplification reaction, such as amplified DNA produced using the polymerase chain reaction (PCR). The nucleic acid material can also be in the form of fragments of DNA produced by digesting DNA with a restriction enzyme. The medium can also be in the form of a mixture of melted or enzymatically digested electrophoresis gel and nucleic acid material.

The silica magnetic particles provided in the second step of the methods of the present invention preferably have the capacity to form a complex with the nucleic acid material in the medium by reversibly binding at least 2 micrograms of nucleic acid material per milligram of particle. The particles provided for use in the present invention more preferably have the capacity to reversibly bind at least 4 micrograms, and more preferably at least 8 micrograms of nucleic acid material per milligram of particle. The silica magnetic particles should preferably have the capacity to release at least 60% of the nucleic acid material adhered thereto. The particles more preferably have the capacity to release at least 70%, and most preferably at least 90% of the nucleic acid material adhered thereto. The silica magnetic particles provided in the first step of the methods of the present invention are most preferably SOCM particles.

A complex of the silica magnetic particles and the biological target material is formed in the third step, preferably by exposing the particles to the medium containing the target material under conditions designed to promote the formation of the complex. The complex is more preferably formed in a mixture of the silica magnetic particle, the medium, and a chaotropic salt.

Chaotropic salts are salts of chaotropic ions. Such salts are highly soluble in aqueous solutions. The chaotropic ions provided by such salts, at sufficiently high concentration in aqueous solutions of proteins or nucleic acids, cause proteins to unfold, nucleic acids to lose secondary structure or, in the case of double-stranded nucleic acids, melt (i.e., strand-separate). It is thought that chaotropic ions have these effects because they disrupt hydrogen-bonding networks that exists in liquid water and thereby make denatured proteins and nucleic acids thermodynamically more stable than their correctly folded or structured counterparts. Chaotropic ions include guanidinium, iodide, perchlorate and trichloroacetate. Preferred in the present invention is the guanidinium ion. Chaotropic salts include guanidine hydrochloride, guanidine thiocyanate (which is sometimes referred to as guanidine isothiocyanate), sodium iodide, sodium perchlorate, and sodium trichloroacetate. Preferred are the guanidinium salts, and particularly preferred is guanidine hydrochloride.

The concentration of chaotropic ions in the mixture formed in this practice of the present method is preferably between about 0.1 M and 7 M, but more preferably between about 0.5 M and 5 M. The concentration of chaotropic ions in the mixture must be sufficiently high to cause the biological target material to adhere to the silica magnetic particles in the mixture, but not so high as to substantially denature, to degrade, or to cause the target material to precipitate out of the mixture. Proteins and large molecules of double-stranded DNA, such as chromosomal DNA, are stable at chaotropic salt concentrations between 0.5 and 2 molar, but are known to precipitate out of solution at chaotropic salt concentrations above about 2 molar. See, e.g. U.S. Pat. No. 5,346,994 issued to Piotr Chomczynski, column 2, lines 56–63. Contrastingly, RNA and smaller molecules of DNA such as plasmid DNA, restriction or PCR fragments of chromosomal DNA, or single-stranded DNA remain undegraded and in solution at chaotropic salt concentrations between 2 and 5 molar.

With any chaotropic salt used in the invention, it is desirable that the concentration of the salt, in any of the solutions in which the salt is employed in carrying out the invention, remain below the solubility of the salt in the solution under all of the conditions to which the solution is subjected in carrying out the invention.

In a practice of the present methods, the mixture formed as described above is incubated until at least some of the nucleic acid material is adhered to the silica magnetic particle to form a complex. This incubation step is carried out at a temperature of at least 0° C., preferably at least 4° C., and more preferably at least 20° C., provided that the incubation temperature is no more than 67° C. The incubation step must be carried out at a temperature below the temperature at which the silica magnetic particles begin to loose their capacity to reversibly bind the nucleic acid material. The incubation step is most preferably carried out at about room temperature (i.e at about 25° C.).

The complex is removed from the mixture using a magnetic field. Other forms of external force in addition to the magnetic field can also be used to isolate the biological target substance according to the methods of the present invention after the initial removal step. Suitable additional forms of external force include, but are not limited to, gravity filtration, vacuum filtration and centrifugation.

The external magnetic field used to remove the complex from the medium can be suitably generated in the medium using any one of a number of different known means. For example, one can position a magnet on the outer surface of a container of a solution containing the particles, causing the particles to migrate through the solution and collect on the inner surface of the container adjacent to the magnet. The magnet can then be held in position on the outer surface of the container such that the particles are held in the container by the magnetic field generated by the magnet, while the solution is decanted out of the container and discarded. A second solution can then be added to the container, and the magnet removed so that the particles migrate into the second solution. Alternatively, a magnetizable probe could be inserted into the solution and the probe magnetized, such that the particles deposit on the end of the probe immersed in the solution. The probe could then be removed from the solution, while remaining magnetized, immersed into a second solution, and the magnetic field discontinued permitting the particles go into the second solution. Commercial sources exist for magnets designed to be used in both types of magnetic removal and transfer techniques described in general terms above. See, e.g. MagneSphere® Technology Magnetic Separation Stand or the PolyATract® Series 9600™ Multi-Magnet, both available from Promega Corporation; Magnetight Separation Stand (Novagen, Madison, Wis.); or Dynal Magnetic Particle Concentrator (Dynal, Oslo, Norway).

In a preferred aspect of the methods of the present invention, the complex removed from the medium in the third step is washed at least once by being rinsed in a wash solution. The wash solution used in this preferred additional step of the method preferably comprises a solution capable of removing contaminants from the silica magnetic particle. The wash solution preferably comprises a salt and a solvent, preferably an alcohol. The concentration of alcohol in this last preferred form of the wash solution is preferably at least 30% by volume, more preferably at least 40% by volume, and most preferably at least 50% by volume. The alcohol so used is preferably ethanol or isopropanol, more preferably ethanol. The salt is preferably in the form of a buffer, and most preferably in the form of an acetate buffer. The concentration of salt in the wash solution is sufficiently high to ensure the nucleic acid material is not eluted from the silica magnetic particles during the wash step(s).

The complex is preferably washed after removal from the medium by resuspending the complex in the wash solution. The complex is preferably removed from the wash solution after the first wash, and washed at least once more, and most preferably three more times using fresh wash solution for every wash step.

Fourth, and finally, the nucleic acid material is eluted from the silica magnetic particle by exposing the complex to an elution solution. The elution solution is preferably an aqueous solution of low ionic strength, more preferably water or a low ionic strength buffer at about a pH at which the nucleic acid material is stable and substantially intact. Any aqueous solution with an ionic strength at or lower than TE buffer (i.e. 10 mM Tris-HCl, 1 mM ethylenediamine-tetraacetic acid (EDTA), pH 8.0) is suitable for use in the elution steps of the present methods, but the elution solution is preferable buffered to a pH between about 6.5 and 8.5, and more preferably buffered to a pH between about 7.0 and 8.0. TE Buffer and distilled or deionized water are particularly preferred elution solutions for use in the present invention. The low ionic strength of the preferred forms of the elution solution described above ensures the nucleic acid material is released from the particle. Other elution solutions suitable for use in the methods of this invention will be readily apparent to one skilled in this art.

The nucleic acid material eluted from the complex in the elution step of the method is preferably separated from the silica magnetic particles and complexes remaining in the elution mixture by external force, such as centrifugation or a magnetic field, but more preferably using centrifugation. Centrifugation is preferred because it can result in the removal of particles or particle fragments which are too small or which are not sufficiently magnetically responsive to be removed by using a magnetic field.

The nucleic acid material eluted using the method of the present invention is suitable, without further isolation, for analysis or further processing by molecular biological procedures. The eluted nucleic acid can be analyzed by, for example, sequencing, restriction analysis, or nucleic acid probe hybridization. Thus, the methods of the invention can be applied as part of methods, based on analysis of DNA or RNA, for, among other things, diagnosing diseases; identifying pathogens; testing foods, cosmetics, blood or blood products, or other products for contamination by pathogens; forensic testing; paternity testing; and sex identification of fetuses or embryos.

The eluted DNA or RNA provided by the method of the invention can be processed by any of various exonucleases and endonucleases that catalyze reactions with DNA or RNA, respectively, and, in the case of DNA, can be digested with restriction enzymes, which cut at restriction sites present in the DNA. Restriction fragments from the eluted DNA can be ligated into vectors and transformed into suitable hosts for cloning or expression. Segments of the eluted DNA or RNA can be amplified by any of the various methods known in the art for amplifying target nucleic acid segments. If eluted DNA is a plasmid or another type of autonomously replicating DNA, it can be transformed into a suitable host for cloning or for expression of genes on the DNA which are capable of being expressed in the transformed host. Plasmid DNAs isolated by methods of the present invention have been found to be more efficiently transfected into eukaryotic cells than those isolated by the prior art method, wherein diatomaceous earth is employed in place of the silica gel in the methods of the invention of this application.

The following, non-limiting examples teach various embodiments of the invention. In the examples, and elsewhere in the specification and claims, volumes and concentrations are at room temperature unless specified otherwise. Only the most preferred form of the magnetic silica particles was used in used in each of the examples below, i.e. SOCM particles. However, one skilled in the art of the present invention will be able to use the teachings of the present disclosure to select and use forms of the magnetic silica particles other than the SOCM particles whose use is illustrated in the aspects of the methods of the present invention demonstrated in the Examples below.

The same batch of SOCM particles was used to produce the assay results presented in Examples 1 and 6 below, while a second batch of SOCM particles was used to generate the results presented in Examples 2–4 and 7. However, both batches of SOCM particles were found to produce acceptable results when tested as described below. The first batch of SOCM particles, i.e. the particles used in Examples 1 and 6, were found to have the following physical characteristics: surface area of 55 m$^2$/g, pore volume of 0.181 ml/g for particles of <600 Å diameter, pore volume of 0.163 ml/g for particles of >600 Å diameter, median particle size of 5.3 $\mu$m, and iron leach of 2.8 ppm when assayed as described herein above using ICP. The other batch of SOCM particles used in the Examples below were found to have the following characteristics: surface area of 49 m$^2$/g, pore volume of 0.160 ml/g (<600 Å diameter), pore volume of 0.163 ml/g (>600 Å diameter), median particle size of 5.5 $\mu$m, and iron leach of 2.0 ppm.

EXAMPLE 1

Assay of Binding Capacity and Elution Efficiency of Silica Magnetic Particles for Plasmid DNA The binding capacity of the SOCM form of silica magnetic particles and of magnetic controlled pore glass (CPG) particles was determined by titrating increasing amounts of plasmid against a constant amount of particles in a final 600 $\mu$l volume of 4.16M guanidine hydrochloride (GHCl). The magnetic CPG particles used were 5 $\mu$M magnetic glass particles with a 500 Å average pore size, obtained from CPG Inc., Lincoln Park, N.J., U.S.A., Part Number MCPG0510).

In the present example, a 140 mg of magnetic silica was suspended in 10 ml of deionized water (DI H$_2$O) and then washed 3 times with 10 ml of 5M GHCl before being suspended at a final concentration 14 mg/ml in the same solution. A binding mixture was formed by adding increasing volumes pGEM200 3zf(+) plasmid DNA from Promega Corporation (Catalog Number P2271) in DI H$_2$O at a concentration of 1.0 micrograms ($\mu$g) per $\mu$l, corresponding to 5 µg, 10 µg, 20 µg, 40 µg, 60 µg and 80 µg of DNA, to 500 µl of the particles and brought to a final volume of 600 µl by the addition of DI H$_2$O. The plasmid/particle binding mixture was then incubated for 2–3 minutes at room temperature.

The amount of plasmid bound to the magnetic silica was determined by subtracting the amount plasmid DNA remaining in solution from the total amount of plasmid added to the particles in each sample, as follows. The liquid fraction of the assay mixture was separated from the magnetic silica by centrifugation at 14,000×g for 20 seconds. The amount of plasmid DNA remaining in the supernatant was determined by monitoring the absorbency of the solution at 260 nm. One absorbency unit at 260 nm is equivalent to a plasmid DNA concentration of 50 µg/ml.

The silica magnetic particles remaining in the binding mixture were then separated from the mixture and washed as follows. A magnet was positioned outside the container holding the binding mixture but close to one side of the container, causing the silica magnetic particles in the mixture to deposit on the side of the container closest to the magnet. The magnet was then maintained in its position on the side of the container while the mixture was decanted out of the container, leaving the substantially all the silica magnetic particles in the container. The remaining silica magnetic particles where then washed 4 times with 1 ml of a wash solution of 80 mM KOAc and 10 µM EDTA containing 55% EtOH, removing the magnet from the side of the container during each washing step and positioning the magnet, once again, on a side of the container to ensure the particles remain in the container while the wash solution is decanted following each washing step. The particles remaining in the container after the last wash step were then air dried for 3–5 minutes.

Finally, the plasmid DNA was eluted from the silica magnetic particles by adding 1 ml of DI water at room temperature. The particles were removed from the resulting isolated plasmid DNA solution by centrifugation. The amount of plasmid DNA eluted was then determined by measuring the absorbency of the solution at 260 nm.

The overall efficiency of the plasmid isolation process was determined as the percent of DNA recovered in the final elution compared to the amount of DNA incubated with the particle. The binding capacity was determined at the point where the overall efficiency dropped to 90%.

Figure 3:
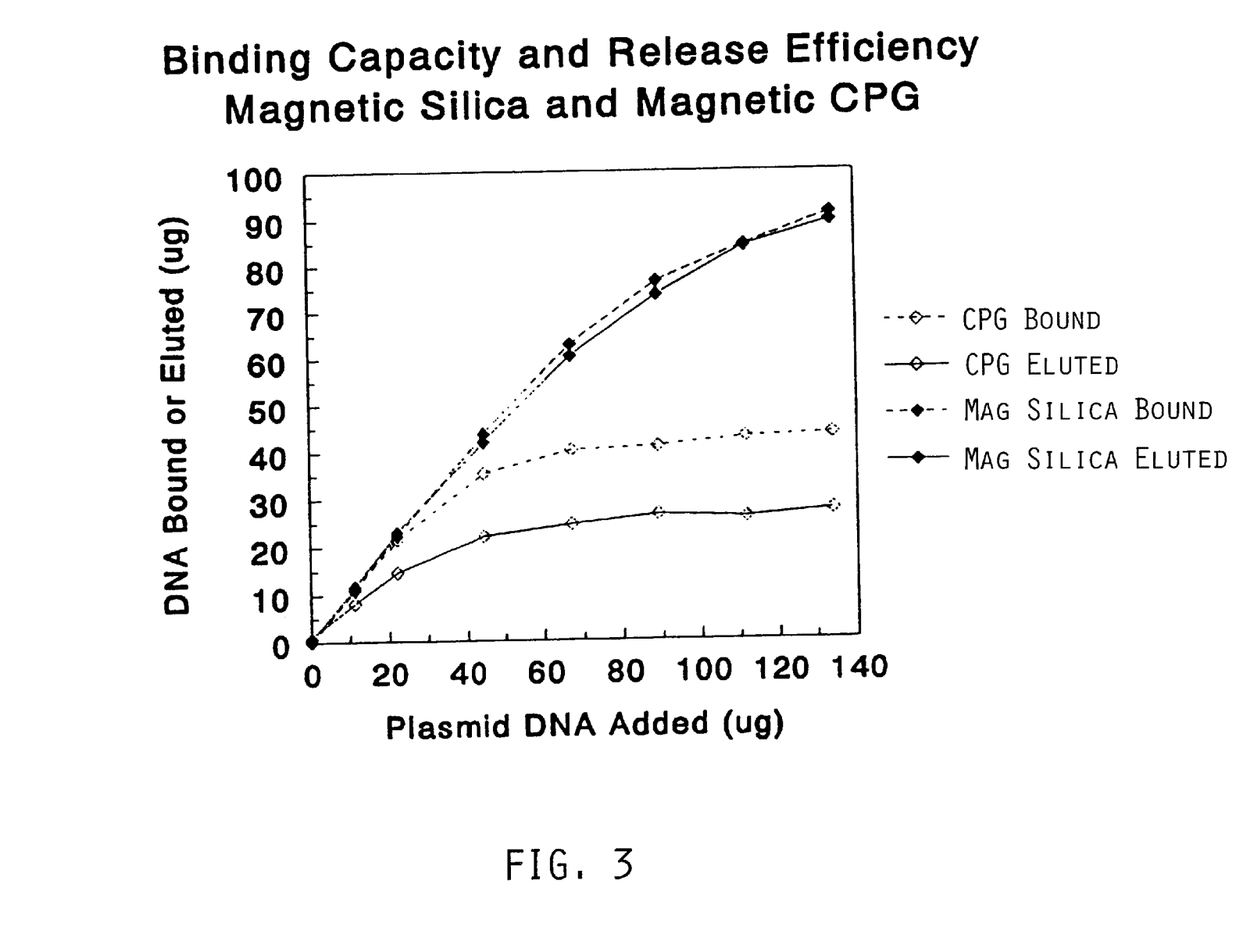
FIG. 3 is a plot of the binding data shown in FIG. 1 and the elution data shown in FIG. 2 obtained from magnetic CPG and silica magnetic particles.

The results of the binding assay described above are presented in FIG. 1, and together with the elution results in FIG. 3. The DNA binding capacity results obtained with the magnetic silica (Δ) and magnetic CPG (+) particles are shown separately in FIG. 1. The results show that as increasing amounts of plasmid DNA was added to the magnetic silica particles, the particles continued to bind increasing amounts of DNA, binding as much as 90 µg per 130 µg of plasmid added. Contrastingly, the magnetic CPG particles failed to bind more than 40 µg of plasmid DNA even when 130 µg of plasmid DNA was added. The total binding capacity of the silica magnetic particles was 8 µg of plasmid per mg of particle. This is significantly higher than the binding capacity of the magnetic CPG particles, and at least 4-fold higher than the binding capacity of the 10 µM silica bead used in Promega Corporation's Wizard™ Plus Plasmid DNA Purification Systems.

The results of the elution assay described above are presented in FIG. 2, and together with the elution results in FIG. 3. The results show that greater than 90% of the plasmid DNA bound to the silica magnetic particles in this example was eluted from the particles, while less than 60% of the plasmid DNA bound to the CPG particles was eluted therefrom.

Figure 1:
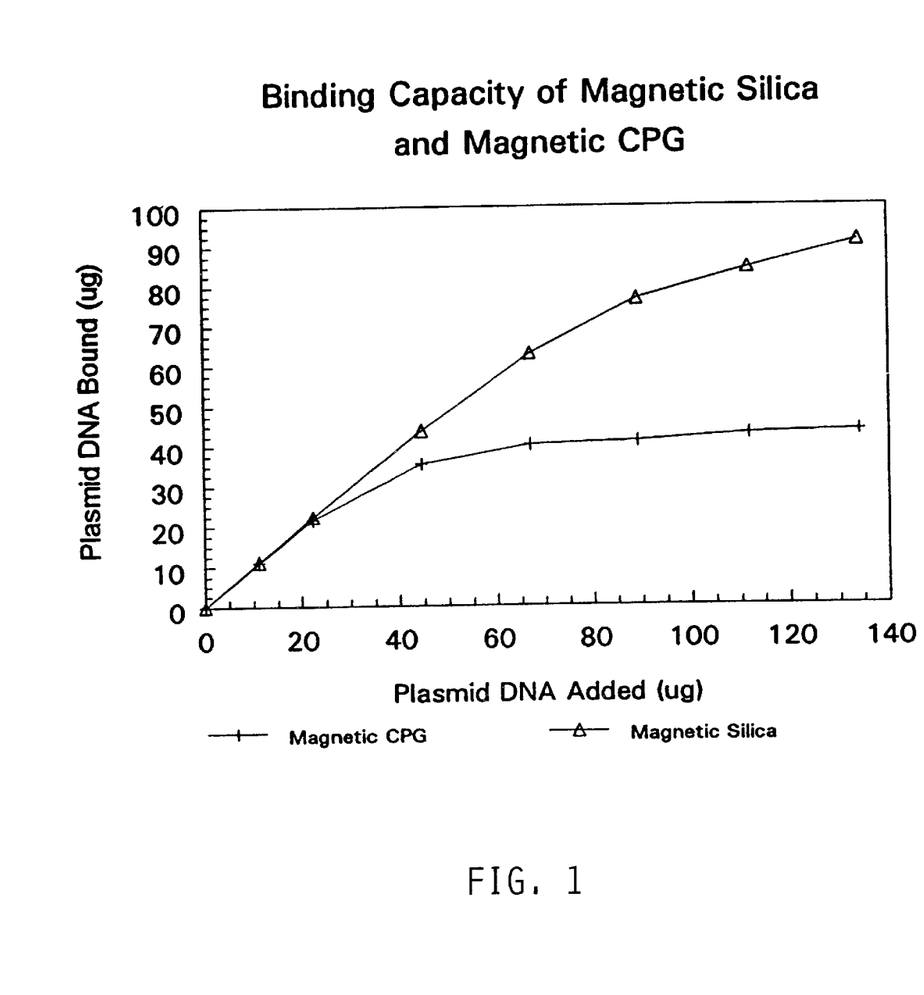
FIG. 1 is a plot of the number of micrograms of plasmid DNA bound per microgram of plasmid DNA added to either magnetic controlled pore glass (CPG) particles or to silica magnetic particles.
Figure 2:
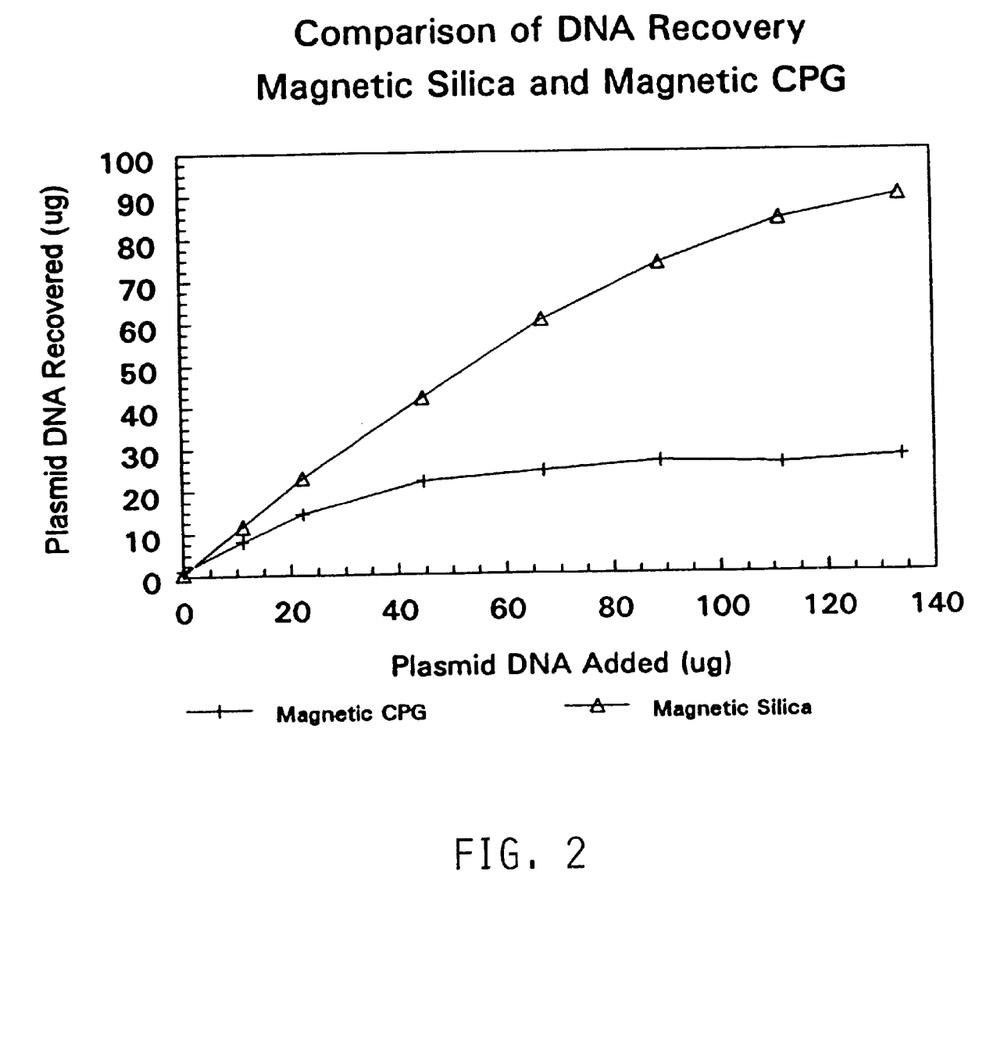
FIG. 2 is a plot of the number of micrograms of plasmid DNA eluted from either magnetic CPG or silica magnetic particles versus the amount of plasmid DNA added to the particles prior to elution.

The results displayed in FIGS. 1–3 clearly demonstrate that the silica magnetic particles assayed herein exhibit excellent binding and elution characteristics.

EXAMPLE 2

Assay of Binding Capacity and Elution Efficiency of Silica Magnetic Particles for DNA Fragments Purified native lambda DNA from Promega Corporation (Catalog Number D150) was digested with Hind III restriction enzyme, an enzyme which cuts native lambda DNA into 8 fragments ranging in size from 23,000 bp to 125 bp. This Hind III digested lambda DNA is referred to hereinafter as "λHind III digest."

The magnetic silica was prepared as described previously and resuspended in 5M GHCl at a concentration of 14 mg/ml. One ml of the resuspended particle solution was incubated with 80 µl of the λHind III digest (0.44 µg/µl) for 2–3 minutes at room temperature. The amount of DNA bound to the magnetic silica was determined by subtracting the DNA remaining in solution from the total amount of DNA added to the particles after separation of the liquid and solid phases by centrifugation at 14,000×g for 20 seconds. DNA concentrations were determined by absorbency measurement at 260 nm. One absorbency unit at 260 nm is equivalent to a DNA concentration of 50 µg/ml.

The silica magnetic particles remaining in the binding mixture were then separated from the mixture and washed as follows. A magnet was positioned outside the container holding the binding mixture but close to one side of the container, causing the silica magnetic particles in the mixture to deposit on the side of the container closest to the magnet. The magnet was then maintained in its position on the side of the container while the mixture was decanted out of the container, leaving the substantially all the silica magnetic particles in the container. The remaining silica magnetic particles where then washed 4 times with 1 ml of a wash solution of 80 mM KOAc and 10 µM EDTA containing 55% EtOH, removing the magnet from the side of the container during each washing step and positioning the magnet, once again, on a side of the container to ensure the particles remain in the container while the wash solution is decanted following each washing step. The particles remaining in the container after the last wash step were then air dried for 3–5 minutes.

Finally, the λHind III digest was eluted by adding 200 µl of DI water at room temperature. The particles were removed from the resulting isolated λ digest solution by centrifugation. The amount of λHind III digest DNA eluted was then determined by measuring the absorbency of the solution at 260 nm.

Similar silica magnetic particle binding and elution assays were performed using φX174 DNA digested with Hae III restriction enzyme, a digestion reaction which produces 10 DNA fragments ranging from 1353 bp to 72 bp in size. The data for these experiments are summarized in Table 1, below.

TABLE 1

| DNA Type | DNA Added | DNA Bound | DNA Eluted* | % Recovery** |
|---|---|---|---|---|
| λ HindIII Digest | 35.0 μg | 33.6 μg | 28.4 μg | 81.0% |
| φX174 HaeIII Digest | 40.0 μg | 39.4 μg | 33.7 μg | 84.2% |

*A second elution step wherein 200 μl of DI water was added to the silica magnetic particles after the first elution step resulted in >97% recovery of bound DNA
**Based on amount of input DNA

EXAMPLE 3

Electrophoresis of DNA Fragments After Elution From Silica Magnetic Particles In order to determine whether the silica magnetic particles bound or released DNA fragments of different molecular weights at different weights, the DNA fragments bound to and eluted from the silica magnetic particles in Example 2 were assayed using electrophoresis as follows. Samples of λHind III digest eluted from two different samples of silica magnetic particles were loaded and fractionated on an agarose gel along with a control sample of untreated DNA digest. Samples of bound and eluted φX174 Hae III digest were also fractionated on an agarose gel along with a control sample of untreated DNA digest. The resulting gels of fractionated DNA were then stained with a fluorescent dye capable of staining DNA, and the stained gels analyzed using a Molecular Dymanics Fluoroimager. The fluorescent intensity of the eluted DNA fragments from each of the restriction enzyme digests were compared to the control digests prior to capture and elution on magnetic silica.

Figure 4:
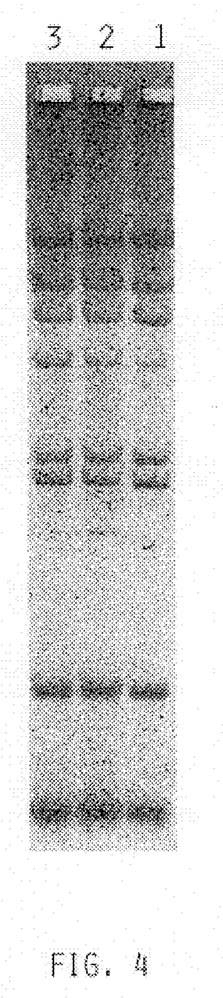
FIG. 4 is a fluorimage of an agarose gel stained with a fluorescent dye, after fractionation of DNA fragments on the gel using gel electrophoresis, wherein the DNA fragments were produced by digesting lambda DNA with Hind III and by binding and eluting the fragments from silica magnetic particles.
Figure 5:
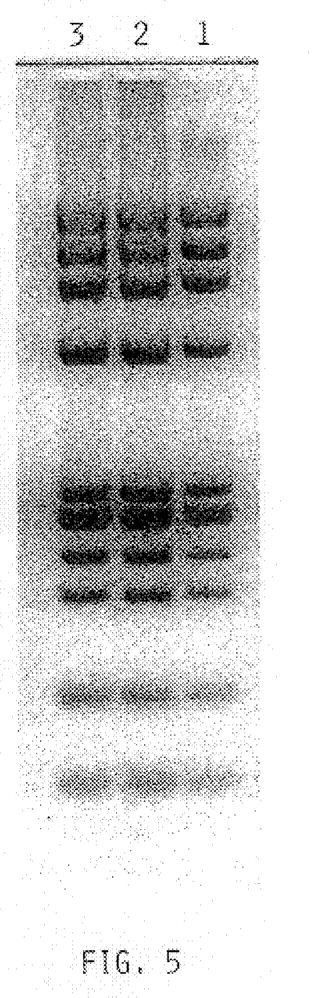
FIG. 5 is a fluorimage of an agarose gel stained with a fluorescent dye, after fractionation of DNA fragments on the gel using gel electrophoresis, wherein the DNA fragments were produced by digesting φX174 DNA with Hae III and by binding and eluting the fragments from silica magnetic particles.

FIGS. 4 and 5 show the visual image generated by the fluorometer from the fluorescent stained agarose gel of fractionated captured and eluted DNA fragments produced as described above. FIG. 4 shows 2 μg of λHindIII digest electrophoesed on 1% agarose gel. FIG. 5 shows 5 μg of φX174 Hae III digest electrophoesed on 3% agarose gel. In both panels, sample 1 is the control of untreated DNA digest, while samples 2 and 3 are samples of digest DNA bound to and eluted from two different samples of silica magnetic particles.

No substantial difference in relative band intensity or background was noted between the control and samples from either set of digest samples analyzed herein, indicating the silica magnetic particles assayed herein do not selectively bind or release DNA fragments according to molecular weight.

EXAMPLE 4

Isolation of Plasmid DNA From Bacterial Cultures Using Silica Magnetic Particles and Magnetic Force Some of the resuspended silica magnetic particles prepared in Example 1 were used to isolate pGEM®-3zf(+) plasmid DNA from a culture of DH5α E. coli bacteria transformed with either form of plasmid DNA. The following solutions were used in the isolation procedure:

1. Cell Resuspension Solution:
   50 mM Tris-HCl, pH 7.5
   10 mM EDTA
   100 μg/ml DNase-free ribonuclease A (RNase A)
2. Column Wash Solution:
   Prepared by making an aqueous buffer consisting of either 200 mM NaCl, 20 mM Tris-HCl, 5 mM EDTA, pH 7.5, or
   190 mM KOAc, 20 mM Tris-HCl, 0.1 mM EDTA, pH 7.5, and by diluting the aqueous buffer 1:1.4 with 95% ethanol (EtOH).
3. TE Buffer:
   10 mM Tris-HCl, pH 7.5
   1 mM EDTA
4. Neutralization Solution:
   1.32M KOAc (potassium acetate), pH 4.8
5. Cell Lysis Solution:
   0.2M NaOH
   1% SDS (sodium dodecyl sulfate)

The bacteria culture was treated to produce a cleared lysate, by following the steps described briefly below:

1. The cells from 1 to 3 ml of bacteria culture were harvested by centrifuging the culture for 1–2 minutes at top speed in a microcentrifuge. The harvested cells were resuspended in 200 μl of Cell Resuspension Solution, and transferred to a microcentrifuge tube. The resulting solution of resuspended cells was cloudy.
2. 200 μl of Cell Lysis Solution was then added to the solution of resuspended cells and mixed by inversion until the solution became relatively clear, indicating the resuspended cells had lysed.
3. 200 μl of Neutralization Solution was added to the lysate solution, and mixed by inversion. The lysate became cloudy after the Neutralization Solution was added.
4. The solution was then spun in a microcentrifuge at top speed for 5 minutes to clear the lysate.
5. The resulting supernatant of cleared lysate was transferred to a new microcentrifuge tube.

Plasmid DNA was then isolated from the cleared lysate using the silica magnetic particles suspended in a solution of guanidine hydrochloride prepared in Example 1. Essentially the same procedure was used to isolate the plasmid DNA using the particles and magnetic force, as was used in the plasmid binding assay described in Example 2. However, the present isolation procedure was initiated by adding 1 ml of the suspended silica magnetic particles to the cleared lysate produced from step 5, immediately above, rather than beginning the procedure by adding 500 μl of suspended particles to 5 to 80 μg of purified plasmid DNA. The volumes of each solution added to the magnetic silica particles at each subsequent step of the present isolation procedure followed were adjusted proportionately to account for the larger starting volume.

The resulting isolated plasmid DNA was assayed qualitatively using gel electrophoresis, and quantitatively using a spectrophotometer. the gel assay results showed a high percentage of intact, supercoiled plasmid DNA present in the sample. The optical density measurements accurately reflected DNA yield, as evidenced by absorbance ratios (ex. 260/250 nm and 260/280 nm) in the expected range for DNA.

EXAMPLE 5

Isolation of Plasmid DNA From Bacterial Cultures Using Silica Magnetic Particles and Vacuum Filtration The same procedure is used to produce a cleared lysate of a culture of E. coli bacteria transformed with plasmid DNA, such as the cleared lysate production procedure used in Example 4. The plasmid is then isolated from the resulting cleared lysate using the suspension of silica magnetic particles of Example 1, but using vacuum filtration rather than magnetic force to separate the particles from the binding mixture once the plasmid DNA has adhered to the particles. Vacuum filtration is also used to remove the wash solution from the particles in the washing steps of the isolation procedure.

EXAMPLE 6

Illustrating Binding of RNA

Using magnetic silica at 14 mg/ml in 4M Guanidine Thiocynate, 700 µl of resuspended silica magnetic particles prepared as in Example 1 were added to 30 µl of Promega RNA Markers, catalog #1550, labeled with $^{32}$P (app. 200,000 cpms), and 5 µl of a 1 mg/ml solution of cold (i.e. unlabeled) Promega RNA Markers part #G3191 in a container.

The resulting mixture was incubated for 5 minutes at room temperature, after which the particles were captured, using magnetic force to draw the particles to one side of the container while the supernatant was decanted into a second container.

The supernant collected in the second container was saved and counted.

The captured particles in the first container were then washed three times with Column Wash Solution, prepared as described in Example 4, above. The particles were captured after each wash step, and the wash solution decanted. Each decanted wash solution was saved and counted. The sum of the supernant counts and the wash void counts was used to determine the total unbound CPMs.

After the third wash step, the RNA was eluted from the captured and washed particles by resuspending the particles in 250 µl of Nanopure water heated to 37° C., and then using magnetic force to hold the particles on the side of the container while the eluent was decanted and collected. 100 µl of the eluent was then counted.

The remaining particles were resuspended in 500 µl of Nanopure water and then counted to determine the amount of uneluted CPMs remaining.

Figure 6:
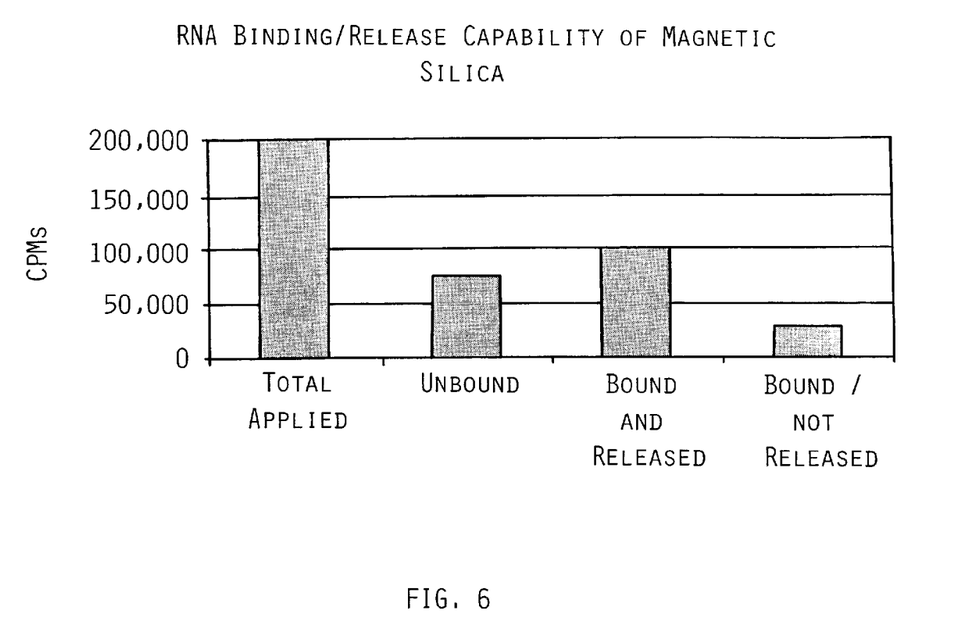
FIG. 6 is a histogram plot of the number of counts per million (CPM) of $^{32}$P-labeled RNA applied to, bound to, and released from silica magnetic particles.

The above analysis was run in duplicate. The results shown in FIG. 6 reflect the counts averaged for each set of duplicates and counts collected in each experiment. FIG. 6 shows that of 200,000 CPMs of RNA exposed to the magnetic silica particles in this assay, an average of 125,000 CPMs became bound to the particles, and about 100,000 of the CPMs bound to the particles was released and eluted from the particles in the final elution step.

These RNA binding and elution assay results are comparable to the DNA binding and elution results described in Example 2, above. The present assay shows the potential application of the magnetic silica particles according to the methods of the present invention to isolate RNA.

EXAMPLE 7

Analysis of Iron Leach From Silica Magnetic Particles

Silica magnetic particles, such as those used in the Examples above, were screened for their tendency to leach iron or other materials likely to interfere with the quantitative analysis of nucleic acid materials, by producing an absorbance peak at or around 260 nm when solutions exposed to the particles are analyzed with a spectrophotometer.

The silica magnetic particles were analyzed as follows. 140 mg of silica magnetic particles were resuspended in 10 ml of DI water and vortexed briefly. The particles were exposed to a magnetic field for 1 minute, by placing a magnet against the outside of the container holding the particle/water mixture. Particles in the mixture collected on the side of the container closest to the magnet surface, and were held against the side of the container by the magnet while the supernatant was decanted out of the container. The magnet was then removed, and the particles remaining in the container were resuspended in another 10 ml of DI water. The collection, decanting, and resuspension steps were repeated three times.

After the third such step, the resuspended particles were sequentially washed twice with 10 ml each of 7M guanidine hydrochloride, pH 5.9, twice with 10 ml of DI water, and twice with 10 m. of 50 mM EDTA (pH 8.0). The supernatants from each of these washes were scanned from 230 nm to 300 nm using a Hewlett Packard Diode array spectrophotometer blanked against each of the control solutions.

No absorbance above background at 260 nm was observed in any of the wash solutions obtained by assaying the silica magnetic particles used in the Examples above.

EXAMPLE 8A

Preparation of Superparamagnetic Iron Oxide Particles

Portions of $FeCl_3$ and $FeCl_2$ were dissolved in deionized water at ambient temperature to form a solution containing 3.24 wt. % $FeCl_3$ and 1.5 wt. % $FeCl_2$. Under strong agitation, a 14 wt. % $NH_4OH$ aqueous solution was quickly added to the solution until a pH of 8.5 was achieved. As a result of the ammonium hydroxide addition, a fine magnetite precipitate ($Fe_3O_4$) was formed. The precipitate was allowed to settle. The most of the liquid component of the mixture was then removed by decantation. The remaining wet precipitate was then reslurried in deionized water to wash the precipitate. This wash procedure was repeated a total of three times to reduce the level of ammonium and chlorine ions. Drying of the precipitate was avoided.

EXAMPLE 8B

Hydrogen Peroxide Treatment of Superparamagnetic Particles 75 g of the magnetite from Example 8A was reslurried in deionized water to achieve a 7.5 wt. % solids concentration. The resulting slurry was agitated and ultrasonically treated while 600 ml of 3 wt. % $H_2O_2$ solution was added to the slurry. The resulting mixture was maintained in this condition for 60 minutes, and then the magnetite was separated from the solution by decantation while drying of the magnetite was avoided. The magnetite was then subjected to three washes, each using 2000 ml deionized water.

EXAMPLE 9

75 g of wet magnetite particles prepared according to Example 8B (based on the amount of magnetite present) was then reslurried in deionized water to form a slurry having a solids content of about 7.5 wt. %. The slurry was heated to about 90° C. and subjected to moderate agitation and sonication. An aqueous sodium silicate solution (10.7 wt. % $SiO_2$ and 3.24 wt. % $Na_2O$) was added to the slurry at a rate of 5 ml/mm for about 43 minutes. During this addition, the sonication was maintained for the first 15 minutes only, but the moderate agitation and 90° C. temperature were maintained throughout the addition. The slurry was allowed to age for ten minutes. Then, additional amounts of the sodium silicate solution were added at 5 ml/mm for about 20 minutes while the slurry was maintained under moderate agitation at 90° C. The slurry pH after the silicate addition was about 10. Under moderate agitation at 90° C., 1N HCl was then added to the slurry at a rate of about 12 ml/mm until a pH of about 7.5 was achieved. The slurry was allowed to age under agitation for about 30 minutes at 90° C., and then the particles were allowed to settle.

The liquid component of the settled slurry was decanted off, and the wet particles were then subjected to water washing (2000 ml deionized water) and decantation. The washing/decantation were repeated two additional times. The wet particles remaining after decantation were washed with 450 ml of 3 wt. % $NH_4Cl$ aqueous solution for about 30 minutes followed by a further decantation. The $NH_4Cl$ washing/decantation steps were repeated two additional times and were then followed by three additional series of deionized water washing/decantation steps.

A portion of the resulting wet product was then dried at about 110° C., and the particle size, surface area and pore volume were measured. The median particle size was determined using a Horiba light scattering device. The surface area and pore volume were determined using nitrogen BET. A portion of the dried product was tested for leachability of core metals using the test method described above. The results are given in Table 1 below. The composition of the resulting material is given in Table 3 below.

EXAMPLE 10

75 g of wet magnetite particles prepared according to Example 8B (based on the amount of magnetite present) was then reslurried in deionized water to form a slurry (pH <7) having a solids content of about 7.5 wt. %. While the slurry was heated to about 90° C. and subjected to moderate agitation and sonication, a minor amount of an aqueous sodium silicate solution (10.7 wt. % $SiO_2$ and 3.24 wt. % $Na_2O$) was added at a rate of 5 ml/mm until a slurry pH of about 7.7 was achieved. Then, both sodium silicate solution and 1N HCl were added to the slurry simultaneously for about 43 minutes. The rate of HCl addition was adjusted to maintain the pH at 7.7 given a 5 ml/mm addition rate for the sodium silicate. During this addition, the sonication was maintained for the first 15 minutes only, but the moderate agitation and 90° C. temperature were maintained throughout the addition. The slurry was allowed to age for ten minutes. Then, additional amounts of the sodium silicate solution (5 ml/mm) and HCl were simultaneously added for about 20 minutes while the slurry was maintained under moderate agitation at 90° C. and pH=7.7. The slurry was allowed to age for about 30 minutes at 90° C. under agitation, and then the particles were allowed to settle.

The particles were then subjected to the same washing and testing procedure as described in Example 9 above. The results are reported in Table 2 below. The composition of the resulting material is given in Table 4 below.

TABLE 2

| Example | Surface area ($m^2/g$) | Pore volume (<600 Å diameter) | Pore volume (>600 Å diameter) | Median particle size ($\mu$m) | Iron leach (ppm) |
|---|---|---|---|---|---|
| 9 | 49 | 0.160 | 0.257 | 5.5 | 2.0 |
| 10 | 35 | 0.124 | 0.106 | 8.1 | 3.4 |

EXAMPLE 11

125 g of wet magnetite particles prepared according to Example 8B (based on the amount of magnetite present) was then reslurried in deionized water to form a slurry having a solids content of about 7.5 wt. %. The slurry was heated to about 90° C. and subjected to moderate agitation and sonication. An aqueous sodium silicate solution (10.7 wt. % $SiO_2$ and 3.24 wt. % $Na_2O$) was added to the slurry at a rate of 8.33 ml/mm for about 43 minutes. During this addition, the sonication was maintained for the first 15 minutes only, but the moderate agitation and 90° C. temperature were maintained throughout the addition. The slurry was allowed to age for ten minutes. Then, additional amounts of the sodium silicate solution were added at 8.33 ml/mm for about 20 minutes while the slurry was maintained under moderate agitation at 90° C. The slurry pH after the silicate addition was about 10. Under moderate agitation at 90° C., 1N HCl was then added to the slurry at a rate of about 20 ml/mm until a pH of about 7.5 was achieved. The slurry was then allowed to age under agitation for about 30 minutes at 90° C. and then the particles were allowed to settle.

The particles were then subjected to the same washing and testing procedures as described in Example 9 above. The undried particles were also tested for magnetic separability using the procedure described above. These results are given in Table 3 below. The composition of the resulting material is given in Table 4 below.

EXAMPLE 12

An additional sample was prepared following the same procedure as in Example 11 except that the magnetite particles were prepared according to Example 8A and that the ten minute aging step during the sodium silicate addition was eliminated.

The particles were tested as in Example 11 above. These results are given in Table 2 below. The composition of the resulting material is given in Table 4 below.

EXAMPLE 13

An additional sample was prepared following the same procedure as in Example 2 except that the amount of magnetite particles used was 550 g. The initial slurry volume and the addition rates of sodium silicate and HCl were scaled up in proportion to the increased amount of magnetite used.

The particles were tested as in Example 11 above. These results are given in Table 2 below. The composition of the resulting material is given in Table 4 below.

EXAMPLE 14

125 g of wet magnetite particles prepared according to Example 8A (based on the amount of magnetite present) was then reslurried in deionized water to form a slurry having a solids content of about 7.5 wt. %. The slurry was heated to about 90° C. and subjected to moderate agitation and sonication. An aqueous sodium silicate solution (10.7 wt. % $SiO_2$ and 3.24 wt. % $Na_2O$) was added to the slurry at a rate of 8.4 ml/mm for about 95 minutes. During this addition, the sonication was maintained for the first 15 minutes only, but the moderate agitation and 90° C. temperature were maintained throughout the addition. Under moderate agitation at 90° C. 1N HCl was then added to the slurry at a rate of about 20 ml/mm until a pH of about 7.5 was achieved. The slurry was then allowed to age under agitation for about 30 minutes at 90° C., and then the particles were allowed to settle.

The particles were then subjected to the same washing and testing procedures as described in Example 11 above. These results are given in Table 3 below. The composition of the resulting material is given in Table 4 below.

EXAMPLE 15

37.5 g of wet magnetite particles prepared according to Example 8A (based on the amount of magnetite present) was reslurried in deionized water to form a slurry having a solids content of about 7.5 wt. %. The slurry was heated to about 90° C. and subjected to moderate agitation and sonication. An aqueous sodium silicate solution (10.7 wt. % $SiO_2$ and 3.24 wt. % $Na_2O$) was added to the slurry at a rate of 5 ml/mm for about 43 minutes. During this addition, the sonication, the moderate agitation and 90° C. temperature were maintained. The slurry was allowed to age for ten minutes. Then, additional amounts of the sodium silicate solution were added at 5 ml/mm for about 213 minutes while the slurry was maintained under moderate agitation at 90° C. Sonication was maintained for all but the last 20 minutes of the addition. Under moderate agitation at 90° C., 1N HCl was then added to the slurry at a rate of about 12 ml/mm until a pH of about 7.5 was achieved. The slurry was then allowed to age under agitation for about 30 minutes at 90° C. and then the particles were allowed to settle.

The particles were then subjected to the same washing and testing procedures as described in Example 11 above. These results are given in Table 3 below. The composition of the resulting material is given in Table 4 below.

TABLE 3

| Example | Surface area ($m^2$/g) | Pore volume (<600 Å diameter) | Pore volume (>600 Å diameter) | Median particle size ($\mu$m) | Iron leach (ppm) | % transmission after 40 sec. | % transmission after 600 sec. |
| --- | --- | --- | --- | --- | --- | --- | --- |
| 11 | 55 | 0.181 | 0.163 | 5.3 | 2.8 | 87.7 | 98.3 |
| 12 | 48 | 0.147 | 0.110 | 5.6 | 3.3 | 96.7 | 100 |
| 13 | 56 | 0.188 | 0.142 | 8.0 | 3.7 | 89.9 | 100 |
| 14 | 47 | 0.145 | 0.105 | 6.5 | 2.0 | 99.5 | 100 |
| 25 | 6 | 0.020 | 0.017 | 4.7 | 0.7 | 79.2 | 99.4 |

Particle Composition

From chemical analysis of the materials resulting from the above examples 9–14, the compositions are given in Table 4 below as weight percent (dry, oxide basis).

TABLE 4

| Example | $SiO_2$ | $Fe_3O_4$ | $Na_2O$ |
| --- | --- | --- | --- |
| 9 | 39.1 | 59.7 | 0.19 |
| 10 | 43.1 | 55.2 | 0.11 |
| 11 | 45.6 | 53.1 | 0.16 |
| 12 | 41.6 | 56.1 | 0.12 |
| 13 | 40.6 | 58.0 | 0.10 |
| 14 | 51.3 | 46.5 | 0.15 |
| 15 | 83.6 | 13.6 | 0.25 |

We claim:

1. A kit for isolating a biological target material from a medium, the kit comprising:
    an aliquot of siliceous oxide-coated magnetic particles suspended in an aqueous solution in a first container, the solution comprising a first chaotropic salt, wherein the particles have the capacity to directly and reversibly bind at least 2 micrograms of the biological target material per milligram of particle, wherein the particles have the capacity to release at least 60% of the biological target material.

2. A kit for isolating a biological target material according to claim 1, further comprising:
    a second solution comprising a second chaotropic salt in a second container; and
    a wash solution in a third container.

3. A kit for isolating a biological target material according to claim 2, wherein said second chaotropic salt is a guanidinium chaotropic salt consisting of guanidine hydrocholoride or guanidine thiocyanate.

4. A kit for isolating a biological target material according to claim 2, wherein the wash solution comprises a salt and a solvent.

5. A kit for isolating a biological target material according to claim 4, wherein said solvent is an alcohol.

6. A kit for isolating a biological target material according to claim 5, wherein the wash solution comprises said alcohol in a concentration of at least 30% by volume.

7. A kit for isolating a biological target material according to claim 5, wherein said alcohol is ethanol or isopropanol.

8. A kit for isolating a biological target material according to claim 4, wherein said salt is in the form of a buffer.

9. A kit for isolating a biological target material according to claim 2, further comprising an elution solution in a fourth container.

10. A kit for isolating a biological target material according to claim 9, wherein the elution solution comprises an aqueous solution of low ionic strength buffered to a pH between about 6.5 and 8.5.

11. A kit for isolating biological target material according to claim 2, wherein the first chaotropic salt and the second chaotropic salt are the same.

12. A kit for isolating plasmid DNA from a medium, the kit comprising:
    an aliquot of siliceous oxide-coated magnetic particles suspended in an aqueous solution in a first container, the solution comprising a first chaotropic salt, wherein the particles have the capacity to directly and reversibly bind at least 2 micrograms of the plasmid DNA per milligram of particle.

13. A kit for isolating plasmid DNA according to claim 12, further comprising:
    a wash solution in a second container;
    a resuspension solution in a third container;
    a neutralization solution in a fourth container; and
    a cell lysis solution in a fifth container.

14. A kit for isolating plasmid DNA according to claim 13, wherein the wash solution comprises a salt and a solvent.

15. A kit for isolating plasmid DNA according to claim 14, wherein said solvent is an alcohol.

16. A kit for isolating plasmid DNA according to claim 15, wherein the wash solution comprises said alcohol in a concentration of at least 30% by volume.

17. A kit for isolating plasmid DNA according to claim 16, wherein said alcohol is ethanol or isopropanol.

18. A kit for isolating plasmid DNA according to claim 14, wherein said salt is an acetate buffer.

19. A kit for isolating plasmid DNA according to claim 13, wherein the resuspension solution comprises Tris-HCL, EDTA, and RNase A.

20. A kit for isolating plasmid DNA according to claim 13, wherein the neutralization solution comprises potassium acetate.

21. A kit for isolating plasmid DNA according to claim 13, wherein the cell lysis solution comprises NaOH and SDS.

22. A kit for isolating plasmid DNA according to claim 13, further comprising a solution comprising a second chaotropic salt in a sixth container.

23. A kit for isolating plasmid DNA according to claim 22, wherein said second chaotropic salt is a guanidinium chaotropic salt consisting of guanidine hydrocholoride or guanidine thiocyanate.

24. A kit for isolating plasmid DNA according to claim 22, wherein the first chaotropic salt and the second chaotropic salt are the same.

* * * * *